United States Patent [19]

Lieberman et al.

[11] Patent Number: 5,026,538

[45] Date of Patent: Jun. 25, 1991

[54] METHOD OF TREATING ARTHRITIS, INCLUDING RHEUMATOID ARTHRITIS, WITH 166 HOLMIUM RADIONUCLIDE

[75] Inventors: Ephraim Lieberman, Suffern; Maurice E. Bordoni, Westtown; Alfred K. Thornton, New Hampton, all of N.Y.

[73] Assignee: Cadema Medical Products, Inc., Middletown, N.Y.

[21] Appl. No.: 367,050

[22] Filed: Jun. 16, 1989

Related U.S. Application Data

[60] Division of Ser. No. 7,597, Jan. 28, 1987, Pat. No. 4,849,209, which is a continuation-in-part of Ser. No. 742,402, Jun. 7, 1985, Pat. No. 4,572,464.

[51] Int. Cl.$^5$ ............................ A61K 43/00; A61N 5/10
[52] U.S. Cl. ............................ 424/1.1; 600/3; 600/4; 534/10
[58] Field of Search ............... 424/1.1; 600/3, 4; 534/10

[56] References Cited

U.S. PATENT DOCUMENTS

| | | | |
|---|---|---|---|
| 3,961,038 | 6/1976 | Benes | 424/1.1 |
| 4,752,464 | 6/1988 | Lieberman et al. | 424/1.1 |
| 4,758,429 | 7/1988 | Gordon | 600/5 X |
| 4,849,209 | 7/1989 | Lieberman et al. | 424/1.1 |
| 4,889,707 | 12/1989 | Day et al. | 424/1.1 |
| 4,897,254 | 1/1990 | Simon et al. | 424/1.1 |
| 4,898,724 | 2/1990 | Simon et al. | 424/1.1 |
| 4,906,450 | 3/1990 | Lieberman et al. | 424/1.1 |
| 4,915,932 | 4/1990 | McLaren et al. | 424/1.1 |

OTHER PUBLICATIONS

Hnatonich et al., "Dysprosium-165 Ferric Hydroxide Macro-Aggregates", *J. Nucl. Med.*, 19(3), pp. 303-308.
Sledge et al., Radiation Synovectomy, No. 152 (1984), pp. 37-40.
Sledge et al., Arthritis and Rheumatism, vol. 20(7), pp. 1334-1342 (1977).

*Primary Examiner*—Richard D. Lovering
*Assistant Examiner*—John M. Covert
*Attorney, Agent, or Firm*—Leonard Bloom

[57] ABSTRACT

$^{166}$Holmium in a carrier metallic hydroxide aggregate is disclosed for the treatment of arthritis and, in particular, rheumatoid arthritis. The compound disclosed preferably has a particle size of 1 to 40 microns, Beta energy emissions in the range of 1.76–1.84 MeV, low levels of gamma ray emissions and a radioactive half-life of 26.8 hours. The preferred metallic hydroxide is selected from the group consisting of Ferric Hydroxide, Aluminum Hydroxide, Bismuth Hydroxide, Chromium Hydroxide, Cupric Hydroxide, Manganese Hydroxide and Stannous Hydroxide. Methods are also disclosed for the preparation of the compound, as well as for the methods of its administration to a patient in need thereof.

3 Claims, No Drawings

METHOD OF TREATING ARTHRITIS, INCLUDING RHEUMATOID ARTHRITIS, WITH 166 HOLMIUM RADIONUCLIDE

CROSS-REFERENCE TO RELATED APPLICATIONS

This application is a division of application Ser. No. 007,597 filed Jan. 28, 1987, now U.S. Pat. No. 4,849,209, which is a continuation-in-part of co-pending application Ser. No. 742,402 filed June 7, 1985 (which issued on June 21, 1988 as U.S. Pat. No. 4,572,464) the disclosure of which is incorporated herein in its entirety.

FIELD OF THE INVENTION

The present invention relates to radioactive compounds, methods for the preparation thereof and a method for the treatment of arthritis, including rheumatoid arthritis.

BACKGROUND OF THE INVENTION

Arthritic disorders are the second leading cause of losses in time and earnings in the United States. Approximately six million of all arthritis sufferers are afflicted rheumatoid arthritis. Of these, over fifty percent (50%) ultimately will have involvement of the knee joint, over eighty percent (80%) will involve the hand joint and somewhat smaller percentages will have involvement of other joints such as the ankle, elbow and shoulder.

Rheumatoid arthritis is believed to be an autoimmune disease wherein parts of the body are attacked by antibodies manufactured in the body. These antibodies may be produced in response to viruses present in the body. While the mechanism for rheumatoid arthritis is not defined, it is a systemic disease. When the disease is active, the erythrocyte sedimentation rate (ESR) is elevated and the blood tests positive for rheumatoid factor.

A source of disability for the sufferer of rheumatoid arthritis is an inflammatory response, of unknown origin, in the synovium, or lining, of the afflicted joint. This chronic inflammation, or synovitis, leads to pannus formation and, eventually, destruction of the joint cartilage.

Presently, the primary method of treating rheumatoid arthritis is by use of compounds directed at blocking the inflammatory process. These compounds include aspirin, penicillamine, gold salts and many other ethical drugs. Unfortunately, these attempts are often unsuccessful and the relief provided is temporary at best. In such instances, the primary alternative is the surgical excision of the inflamed synovium in a procedure known as surgical synovectomy. In this procedure the abnormal synovium and pannus formation are surgically removed. While, in many cases, this procedure proves to arrest the disease, it also has a significant number of drawbacks and limitations. Among these are limitations on complete removal of the inflamed synovium, the risks and dangers inherent in the operation itself; and the required lengthy recovery period, much of which is spent in the hospital.

In order to overcome these problems, attempts have been made to destroy the diseased synovium by the performance of a procedure known as radiation synovectomy. Intra-articular injection of colloidial gold-198 ($^{198}Au$) has been reported to abate inflamed synovium (Fellinger et al, 33 WEIN Z. INN, Med. 351, (1952) and Ansell et al, 22 Ann. Rheum. Dis. 435 (1963)). Unfortunately, this procedure is disadvantageous due to the small particle size of the gold colloid utilized and the high energy gamma photons emitted during decay (gamma emission). This emission poses dangers to the patient by increasing the whole body dose, thereby exposing healthy tissue to radiation, and posing substantial difficulties with radiation protection for hospital personnel.

The use of other radionuclides has also been attempted in radiation synovectomy. These radionuclides include Erbium-169 ($^{169}Er$) as reported in Menkes et al, 36 Ann. Rheum. Dis. 254 (1977); Rhenium-186 ($^{186}Re$) as reported in Deckart et al, 3 Radiobiol, Radiother 363 (1979) and in DelBarre et al, 2Nour. Presse. Med 1372 (1973); Phosphorus-32 ($^{32}P$) as reported in Wenston et al, 14 J. Nuc. Med 886 (1973), and Yttrium-90 ($^{90}Y$) as reported in Gumpel et al, 48 Br. J. Radiol. 377 (1975).

Each of these radionuclides ($^{169}Er$, $^{186}Re$, $^{32}P$, $^{198}Au$ and $^{90}Y$) has proven disadvantageous due to either the long physical half-life of the particular radionuclide involved, the small particle size of the system, and/or the occurrence of significant amounts of radioactivity leaking from the affected joints and associated chromosonal abberations in the lymphocytes of the patient. (See also; Oka et al, 17 Acta Rheum. Scand. 148 (1971) and Virkkunen et al, 13 Acta Rheum, Scand, 1967.)

Currently, the preferred radionuclide in the prior art is Dysprosium $^{165}$ ($Dy\ ^{165}$) hyrdroxide in Ferric Hydroxide. Sledge et al, 182 Clin. Ortho, and Rel. Research 37 (1984) (hereinafter referred to as "Sledge"). Sledge has found that the use of $^{65}Dy$ hydroxide in ferric hydroxide is more advantageous in performing radiation synovectomy than the aforementioned radionuclides. Sledge has identified as the advantages of $^{65}Dy$ hydroxide in ferric hydroxide: (1) proper energy range beta emmissions; (2) formation of a larger colloid which reduces the potential of leakage; and (3) an extremely short half-life of 2.3 hours which further reduces the effects of potential leakage.

These are qualities which the prior art has reported to be desirable when selecting an appropriate radioactive compound for use in radiation synovectomy (See also Sledge et al, 20 Arthritis Rheum 1334 (1977), Noble, et al, 65A J. Bone Joint Surg. 381 (1983), and Deckert and Gumpel, both supra).

While the short half-life of $^{165}Dy$ in ferric hydroxide is one of the major characteristics noted by Sledge and the other references which make it such a desirable candidate for radiation synovectomy, this short half-life also proves to be a major limitation to its use. $^{65}Dy$ requires a nuclear reactor in order to be produced. It also must be injected within a few hours of its manufacture to be effective. As a result, its utility in radiation synovectomy is severely limited by geographical and distribution factors.

Accordingly, it is obvious that there remains a need for an effective radioactive compound that will have both utility in radiation synovectomy and will be able to be prepared in, and distributed from, a central location using existing transportation channels.

SUMMARY OF THE INVENTION

According to this invention, certain radioactive compounds have utility in radiation synovectomy for the treatment of rheumatoid arthritis. In accordance with the teachings of this invention, desired factors include: safety, effectiveness, a relatively large particulate carrier, beta emissions of a desired energy and half-life that permits distribution and not high levels of other types of energies which can damage healthy tissue. Also, in accordance with this invention, other desirable physical properties include a radionuclide having a half-life which is both long enough to permit the compound's central preparation and distribution and short enough to reduce the effects of potential leakage.

We have found that compounds having a $^{166}$Holmium radionuclide exhibit the aforementioned physical properties.

Accordingly, it is the primary object of this invention to provide radioactive isotopes in a form useful in the treatment of arthritis and, more particularly, useful for radiation synovectomy in the treatment of rheumatoid arthritis, especially rheumatoid arthritis of the knee.

It is still another object to provide radioactive compounds for the treatment of arthritis, and more particularly, rheumatoid arthritis which can be prepared at, and distributed from, a central location utilizing existing transportation channels.

It is yet still another object of this invention to provide methods for the preparation of radioactive compounds useful in radiation synovectomy for the treatment of rheumatoid arthritis.

It is another object of this invention to provide methods for the treatment of arthritis and, more particularly, rheumatoid arthritis.

These and other objects are accomplished by one or more embodiments made in accordance with the teachings of the present invention.

In accordance with the teachings of the present invention $^{166}$Holmium isotope is provided in a form useful for the treatment of arthritis and, more particularly in a form which are useful for radiation synovectomy in the treatment of rheumatoid arthritis.

In further accordance with the teachings of the present invention, a radioactive compound including $^{166}$Holmium is provided for the treatment of arthritis, and more particularly rheumatoid arthritis, which can be prepared at and distributed from a central location utilizing existing channels of transportation.

In still further accordance with the teachings of the present invention methods for the preparation of radioactive compounds useful in radiation synovectomy for the treatment of rheumatoid arthritis.

In still yet further accordance with the teachings of the present invention, there is provided a method for the treatment of arthritis and, more particularly, rheumatoid arthritis.

The nature and substance of the present invention, as well as its objectives and advantages, will be more clearly perceived and fully understood by reference to the following description and claims.

DESCRIPTION OF PREFERRED EMBODIMENTS

The radioactive compounds of the present invention have particular utility in the treatment of arthritis and, more specifically, in the treatment of rheumatoid arthritis. They also have particular utility for use in radiation synovectomy.

The radioactive compound of the present invention is $^{166}$Holmium nuclide. $^{166}$Holmium has a half-life of 26.8 hours [See Handbook of Chemistry and Physics, 62nd Edition, Chemical Rubber Corporation (1981-1982) at B-302] which allows for sufficient time following production of the isotope in a nuclear reactor for the preparation and distribution of the finished compound using existing transportation channels. $^{166}$Holmium has beta energies up to 1.84 MeV with approximately 85% of the beta parlicles being in the 1.76-1.84 MeV energy range.

While, during decay, $^{166}$Holmium does emit a low energy KeV gamma photon, this emission is not disadvantageous due to its low energy. Additionally, while $^{166}$Holmium also has a high energy gamma emission, this emission is less than 1% in abundance. Therefore, these gamma emissions do not present undue problems to either the patient or hospital personnel.

$^{165}$Holmium, from which $^{166}$Holmium is obtained, has a natural abundance of 100%. The activation cross-section for production of $^{166}$Holmium from $^{165}$Holmium by thermal neutrons permits substantial quantities of Holmium to be produced in a nuclear reactor.

$^{166}$Holmium has an average soft tissue penetration of approximately 3.3 mm and a maximum soft tissue penetration of approximately 9 mm. This beta energy makes Holmium particularly attractive for radiation synovectomy of a diseased knee. We have found that $^{166}$Holmium in certain chemical compounds also forms a substantially large colloid which further reduces the potential for leakage.

The preferred form of $^{166}$Holmium is the hydroxide. However, it is to be understood that the Holmium radionuclide can be suitably formed as any colloidal particle.

The preferred radioactive compound of the present invention is Holmium Hydroxide in a carrier of ferric hydroxide macroaggregate (FHMA). It is to be noted that other compounds such as Holmium Hydroxide in a carrier aluminum hydroxide macroaggregate (AHMA) or Holmium Hydroxide formed in the presence of other soluble transition metal chlorides (i.e. Bismuth and Chromium, to name but two)—which when coverted to the hydroxide forms a metallic hydroxide—would also suffice. In that the particle size of the radioactive compound has a major impact on the leakage rate, the preferred radioactive compound has a minimum particle size of 1 micron. As practiced and prepared herein, the $^{166}$Holmium ferric hydroxide aggregate carrier has a particle size ranging from 1 micron to 40 microns.

While not required, it is preferred that the aggregate suspension further contain a stabilizing ingredient to aid in preventing agglomeration of the particles in the preparation. This stabilizing agents include high molecular weight polymers such as polyvinyl pyrrolidone (PVP). Other high molecular weight polymers such as a polyoxypropylene-polyoxyethylene block-copolymer may be combined with the $^{166}$Holmium macroaggregate.

The radioactive metallic hydroxide aggregate suspension is prepared by a method comprising, first obtaining Holmium in a suitable form. In the preferred embodiment, the starting material is $^{165}$Holmium as a natural oxide ($^{165}$Ho$_2$O$_3$). This suitable form of Holmium is then irradiated in a nuclear reactor to obtain the desired species of the compound. In the preferred embodiment, this reaction is:

$$^{165}\text{Ho} + \text{neutrons} \rightarrow {^{166}}\text{Ho as } {^{166}}\text{Ho}_2\text{O}_3 + \text{gamma photons}$$

Following irradiation, the radionuclide is then dissolved in dilute hydrochloric acid to produce a chloride form of the radionuclide. In the preferred embodiment, this dissolution of the irradiated target oxide proceeds by the following equation:

$$^{166}Ho_2O_3 + (dilute)6HCl \rightarrow 2^{166}CoCl_3 + H_2O.$$

To this solution is then added a solution of a transition metal chloride. In the preferred embodiment, and for purposes of illustration herein, the transition metal chloride described is Ferric Chloride ($FeCl_3$). However, it is to be understood that the transition metal chloride utilized may alternatively be Aluminum Chloride ($AlCl_3$), Bismuth Chloride ($BiCl_3$), Chromium Chloride ($CrCl_3$), Cupric Chlorite ($CuCl_2$), Maganese Chloride ($MnCl_2$) or Stannous Chloride ($SnCl_2$). Sodium Hydroxide is then added to this solution in an amount sufficient to adjust the pH of the solution to a value of from 4 to 9. In the preferred embodiment, the reaction then proceeds according to the following equation:

$$^{166}HoCl_3 + FeCl_3 + 6NaOH \rightarrow {}^{166}Ho(OH)_3 + Fe(OH)_3 + 6NaCl.$$

The product is an aggregated precipitate of the metal (which in this case is Iron) and Holmium Hydroxides which are intimately coprecipitated. The particle size of this precipitate ranges from 1 to 40 microns.

If desired, one may then prepare this aggregated precipitate in order to utilize this compound for the treatment of arthritis and, in particular, of rheumatoid arthritis, by use of one of several asceptic methods during the preparation thereof which are well known to those skilled in the art and by testing for pyrogens by methods which are also well known to those skilled on the art. Preferably, pre-filtration is effected by use of a 0.22 or a 0.45 micron filter.

It is also to be understood by those skilled in the art that certain agents may be added to the original Holmuim Chloride solution. For purposes of illustration only, prior to the addition of the Sodium Hydroxide, a stabilizing matrix such as Polyvinyl Pyrrolidone (PVP) is added to the original Holmium Chloride solution. This stabilizer is added to the suspension to help in maintaining discreet particles (separate particles) to prevent agglomeration of the aggregate.

The $^{166}$Holmium Hydroxide preparation is then ready for being administered to the patient. At this time, the $^{166}$Holmium Hydroxide preparation may be immediately administered or, if desired, it may be suitably packaged and shipped to its ultimate point of use by utilization of existing channels of transportation.

Administration of the $^{166}$Holmium Hydroxide preparation is performed by methods well known to those skilled in the art. By way of example, the preferred method of administration to the knee, hip and/or shoulder of an individual is by intra-articular injection. This administration is exemplified by the following example:

EXAMPLE I

The injection will be performed in the patient's room or in any other suitable location with monitoring by hospital personnel. Patient will be in the supine position.

The knee will be washed with, preferably, a betadine solution. One percent lidocaine hydrochloride will be instilled in the skin and subcutaneous tissue.

A 3-way stopcock/needle assembly will be utilized to administer the compound. A 19 gauge needle will be employed. The suspension of $^{166}$Holmium Hydroxide FHMA will be injected into the joint space using a standard lateral approach well known to those skilled in the art. The needle and needle tract are to be cleansed by flushing with 1% lidocaine hydrochloride through the 3-way stopcock assembly as the needle is withdrawn. The knee will be moved through a flexion-extension arc and then immobilized in full extension. The patient will be confined to bed for approximately 24 hours to minimize movement and minimize leakage of radioactivity from the joint.

It will be understood by those skilled in the art that the exact amount of radioactive compound to administer as a therapeutic agent is also within the skill of the practitioner. However, by way of example, if the practitioner desires to deliver a dose of 10,000 rads to the afflicted synovium, he must merely use classic techniques, well known to those skilled in the art, for Beta dosimetry that assume a homogenous distribution of radioactivity in the synovium without extra-articular leakage in order to arrive at quantity of radioactive compound to administer. We have found that 17.5 mCi of the $^{166}$Holmium Hydroxide preparation will deliver approximately 10,000 rads to the diseased synovium.

The production of the radioactive compound of the present invention requires use of a nuclear reactor. However, production of Holmium$^{166}$ is relatively simple and inexpensive. The half-life of Holmium$^{166}$ facilitates distribution and eliminates logistic problems, as well as problems associated with the ultimate disposal of the compounds, thereby facilitating the widespread commercialization of this invention.

Thus, this invention provides a novel radioactive compound; a method for the preparation of such compound; and a method that is useful in the treatment of arthritis and, more particularly, rheumatoid arthritis, and for alleviating the pain and suffering associated therewith.

While specific embodiments of the present invention have been shown and described to illustrate inventive principles, it is to be understood that such showing and description have been offered only by way of example and not limiting. Protection by Letters Patent of this invention in all its aspects as the same are set forth in the appended claims is sought to the broadest extent that the prior art allows.

What is claimed is:

1. A method for the treatment of arthritis comprising administering an effective amount of a radioactive composition including an aggregated suspension having particles, the particles having a minimum particle size of one micron, the aggregated suspension including particles containing $^{166}$Holmium, to the inflamed synovium of the particular joint of a mammal body in need of such treatment.

2. A method for the treatment of arthritis of an articular joint including skin, subcutaneous tissue and a joint space, said method comprising the steps of:
   preparing an aggregated suspension containing particles, the particles having a minimum particle size of one micron, the aggregated suspension including particles containing $^{166}$Holmium;
   preparing a solution of one percent lidocaine hydrochloride;
   placing the aggregated suspension in a needle assembly having a 19 gauge needle including a needle tract and a three-way stopcock;
   washing the skin of the articular joint with a bentadient solution;
   instilling the lidocaine hydrochloride in the skin and subcutaneous tissue;
   injecting the aggregated suspension into the joint space in a standard lateral approach;

cleansing the needle and needle tract by flushing with one percent lidocaine hydrochloride through the stopcock assembly as the needle is withdrawn;
moving the joint through a flexion-extension arc; and
immobilizing the joint in full extension for approximately 24 hours.

3. A method for the treatment of arthritis of an articular joint comprising: administering a therapeutically effective quantity of an aggregated suspension containing particles, the particles having a minimum particle size of minimum, the aggregated suspension including particles containing $^{166}$Holmium to perform radiation synovectomy.

* * * * *